United States Patent [19]

Hoercher et al.

[11] Patent Number: 5,041,572

[45] Date of Patent: Aug. 20, 1991

[54] PREPARATION OF 2,3,5-TRIMETHYL-P-BENZOQUINONE

[75] Inventors: Ulrich Hoercher, Mannheim; Barbara Jessel, Ludwigshafen; Bernhard Bockstiegel, Limburgerhof; Paul Grafen, Weisenheim; Harald Laas, Maxdorf, all of Fed. Rep. of Germany

[73] Assignee: BASF Aktiengesellschaft, Ludwigshafen, Fed. Rep. of Germany

[21] Appl. No.: 493,103

[22] Filed: Mar. 13, 1990

[30] Foreign Application Priority Data

Mar. 17, 1989 [DE] Fed. Rep. of Germany ....... 3908768

[51] Int. Cl.$^5$ ..................... C07C 50/02; C07C 50/38
[52] U.S. Cl. ..................... 552/310; 552/309
[58] Field of Search ................. 552/309, 310

[56] References Cited

U.S. PATENT DOCUMENTS

| | | | |
|---|---|---|---|
| 3,213,114 | 10/1965 | Braxton et al. | 552/309 |
| 3,796,732 | 3/1974 | Brenner | 552/309 |
| 3,870,731 | 3/1975 | Hutchings | 552/310 |
| 4,202,788 | 5/1980 | Zannucci et al. | 552/309 |
| 4,208,339 | 6/1980 | Costanini et al. | 552/309 |
| 4,522,757 | 6/1985 | Hsu et al. | 552/309 |
| 4,915,875 | 4/1990 | Diephouse et al. | 552/304 |

FOREIGN PATENT DOCUMENTS

| | | |
|---|---|---|
| 0035635 | 9/1981 | European Pat. Off. . |
| 0070665 | 1/1983 | European Pat. Off. . |
| 0093880 | 11/1983 | European Pat. Off. . |
| 0107427 | 5/1984 | European Pat. Off. . |
| 0127888 | 12/1984 | European Pat. Off. . |
| 0167153 | 1/1986 | European Pat. Off. . |
| 0294584 | 12/1988 | European Pat. Off. . |
| 2221624 | 11/1972 | Fed. Rep. of Germany . |
| 2444234 | 4/1975 | Fed. Rep. of Germany . |
| 2827552 | 1/1979 | Fed. Rep. of Germany . |

*Primary Examiner*—C. Warren Ivy
*Assistant Examiner*—Raymond Covington
*Attorney, Agent, or Firm*—Oblon, Spivak, McClelland, Maier & Neustadt

[57] ABSTRACT

2,3,5-Trimethyl-p-benzoquinone is prepared by oxidation of trimethylphenol with oxygen or an oxygen-containing gas in the presence of a catalyst containing a copper(II) halide in a two-phase reaction medium consisting of water and an aliphatic alcohol at elevated temperatures by a process in which the reaction is carried out in a mixture of water and a saturated aliphatic alcohol of 12 to 18 carbon atoms, having a flashpoint greater than 120° C., such as 1-dodecanol, 1-tetradecanol, 1-hexadecanol or 1-octadecanol, in particular 1-dodecanol, and at from 60° to 100° C.

Particularly good yields of TMQ are obtained if the reaction is carried out in the presence of a copper(II) halide, such as $CuCl_2$ or $CuBr_2$, and of an alkaline earth metal halide, in particular $CaCl_2$ or $MgCl_2$, or of an alkali metal halide, in particular LiCl or NaCl, as the catalyst system.

8 Claims, No Drawings

PREPARATION OF 2,3,5-TRIMETHYL-P-BENZOQUINONE

The present invention relates to an improved process for the preparation of 2,3,5-trimethyl-p-benzoquinone (referred to below as TMQ) by oxidation of 2,3,6-trimethylphenol (referred to below as TMP) with gaseous oxygen in the presence of a catalyst containing a copper halide.

TMQ is an important intermediate for the preparation of trimethylhydroquinone, an essential precursor for the synthesis of α-tocopherol (vitamin E).

Because of its considerable importance, there has been no lack of attempts to provide a particularly advantageous process for the preparation of TMQ.

Thus, many methods for the oxidation of TMP and other phenols to the corresponding benzoquinones with oxygen as an oxidizing agent have been disclosed. In the process of German Patent 2,221,624, this is done using copper(II) chloride as the catalyst and dimethylformamide (DMF), ethylene glycol monomethyl ether or acetone, with or without water, as a solvent.

The oxidation of TMP to TMQ can also be carried out after the preparation of TMP from 2,3,6-trimethyl-2-cyclohexen-1-one, as a one-pot reaction. In the process of European Patent 93,880, lower alcohols (in particular isopropanol) are used as solvents for this purpose, while in European Patent 35,635 DMF, acetonitrile, diethylene glycol monomethyl ether or diethylene glycol dimethyl ether are preferably used. In both processes, oxidation is effected with air or oxygen, with catalysis by copper(II) halides.

In the process of German Patent 2,827,552, copper(I) or copper(II) chloride to which elemental metal and an alkali metal or alkaline earth metal halide have been added is used as the catalyst for the oxidation of phenol to p-benzoquinone. Methanol, acetonitrile and DMF are mentioned as solvents. In the processes of European Patents 70,665 and 107,427, the catalyst used is a copper(II) halide, with an alkali metal or alkaline earth metal base as a promoter, and acetonitrile is employed as the solvent.

DE 2 444 234 describes the use of an oxygen partial pressure of up to 52 bar for the oxidation of TMP, a thiocyanate, cyanate or cyanide being added to the copper catalyst in DMF.

EP-A 0 294 584 discloses a process for the preparation of TMQ, in which TMP is oxidized in the presence of an aqueous solution of $CuCl_2$ and $LiCl$ in a mixture of an aromatic hydrocarbon and a lower aliphatic alcohol.

A very good process is that described in European Patent 127,888. Said patent describes a process for the preparation of 2,3,5-trimethyl-p-benzoquinone by oxidation of trimethylphenol with $O_2$ in a 2-phase reaction medium consisting of water and an aliphatic $C_4-C_{10}$-alcohol and in the presence of a copper/alkali metal/halogen complex of the general formula $M_l[Cu(II)_m X_n]_p$, where M is an alkali metal or ammonium, X is a halogen atom, l is an integer from 1 to 3, m and p are each 1 or 2 and n is an integer from 3 to 6, and $1+2mp=n.p$. This process gives good yields of 2,3,5-trimethyl-p-benzoquinone. European Patent 167,153 furthermore discloses a process for the preparation of trimethyl-p-benzoquinone, this process being essentially identical to the process described above, except that copper(I) hydroxide or copper(I) chloride is also added to the catalyst and slow dropwise addition of the alcoholic TMP solution to the aqueous catalyst solution is said to be essential.

An advantage of the three last-mentioned processes is that the catalyst can be readily separated off from the product by carrying out the process in a 2-phase solvent system. A disadvantage of the two last-mentioned processes is that the copper/alkali metal/halogen complex used as a catalyst has to be prepared separately beforehand. A disadvantage of these two processes and of the other known processes is that flammable solvents are used. The danger of explosion in industrial plants due to the use of flammable solvents is usually avoided by carrying out the process under nitrogen In the processes described, however, this is not possible since gaseous oxygen or air is required here as an oxidizing agent.

To ensure safety in the industrial procedure, it is therefore important for the flashpoint of the solvent used to be as far as possible above the reaction temperature in order to exclude the possibility of disastrous explosions. The flashpoint should be so high that no danger of explosion is to be expected even in the event of temperature increases due to a brief uncontrolled reaction or in the event of technical problems in the plant. This is not the case with the processes cited. Table 1 states the flashpoints of the solvents preferably used in the publications cited. The preferred reaction temperatures required for achieving good yields are 60° C. or higher in all cases.

TABLE 1

| Solvent | Flashpoint in °C. |
| --- | --- |
| DMF | 57 |
| Ethylene glycol monomethyl ether | 46 |
| Acetone | −17 |
| Isopropanol | 22 |
| Diethylene glycol monomethyl ether | 83 |
| Acetonitrile | 5 |
| Diethylene glycol dimethyl ether | 70 |
| Methanol | 11 |
| Hexanol | 60 |
| Heptanol | 73 |
| Octanol | 81 |
| Nonanol | 75 |
| Decanol | 82 |

Only the $C_7-C_{10}$-alkanols heptanol, octanol, nonanol and decanol, which can be used as solvents in the processes of European Patents 167,153 and 127,888, have flashpoints slightly above the reaction temperatures of about 60° C. which are preferred there. However, a greater safety margin is desirable for an industrial plant in order to ensure that the danger of explosion is as small as possible.

It is an object of the present invention to provide a process for the catalytic oxidation of TMP to TMQ, in which a solvent having a high flashpoint and a very large difference between the reaction temperature and the flashpoint is used and in which at the same time good yields of TMQ are obtained, the catalyst can readily be prepared and is easy to recover from the reaction mixture and furthermore the boiling point of the solvent differs very greatly to the boiling point of the TMQ, ensuring simple separation by distillation and purification of the TMQ and simple recovery of the solvent.

We have found, surprisingly, that this object is achieved if a mixture of water and a saturated aliphatic alcohol of 12 to 18, preferably 12 to 14, carbon atoms is used as the solvent system, particularly when the catalysts employed are copper(II) halides to which alkaline earth metal or alkali metal halides have been added to increase activity.

This result was unexpected in that the stated alcohols, such as dodecanol, tetradecanol, hexadecanol or octadecanol, are wax-like solids which have hydrophobic properties and substantially lower water solubility than the $C_5$–$C_{10}$-alcohols described in European Patent 127,888. Hence, poorer interactions of the organic phase with the aqueous catalyst solution and therefore less suitability for the stated 2-phase reaction were expected. Surprisingly, however, it was found that the oxidation of TMP to TMQ under the stated conditions takes place very advantageously and does so at temperatures which differ sufficiently greatly from the flashpoint of the particular solvent. Table 2 summarizes some of the alcohols used according to the invention, together with the reaction temperatures preferably employed with them and the flashpoints.

TABLE 2

| Alcohol | Flashpoint | Boiling point | Preferred reaction temperature |
|---|---|---|---|
| Dodecanol | 127° C. | 261° C. | 80° C. |
| Tetradecanol | 141° C. | 289° C. | 80–90° C. |
| Hexadecanol | 135° C. | 180° C./10 mm | 80–90° C. |
| Octadecanol | 192° C. | 170° C./2 mm | 80–90° C. |

Table 2 shows that in all cases the difference between the reaction temperature and the flashpoint is substantially greater than 40° C., so that explosions due to ignition sparks in the gas space are ruled out. The safety margin is substantially greater than in the case of the $C_5$–$C_{10}$-alcohols described in European Patents 127,888 and 167,153. This permits a safe industrial realization of the catalytic oxidation of TMP to TMQ with gaseous oxygen.

Another advantage is the large difference between the boiling points of the alcohols used (cf. Table 2) and the boiling point of the TMQ (198° C.). This permits simple separation of TMQ from the solvent by distillation and simple recovery of the alcohol. Working in a 2-phase system also has the advantage of simple removal and recycling of the aqueous catalyst solution.

The present invention therefore relates to a process for the preparation of 2,3,5-trimethyl-p-benzoquinone by oxidation of trimethylphenol with oxygen or an oxygen-containing gas in the presence of a catalyst containing a copper(II) halide, in a two-phase reaction medium consisting of water and an aliphatic alcohol, at elevated temperatures, wherein the reaction is carried out in a mixture of water and a saturated aliphatic alcohol of 12 to 18 carbon atoms, having a flashpoint greater than 120° C., and at from 60° to 100° C.

Examples of saturated aliphatic alcohols of 12 to 18 carbon atoms, having a flashpoint greater than 120° C., are 1-dodecanol, 1-tetradecanol, 1-hexadecanol and 1 octadecanol, in particular 1-dodecanol.

Good yields of TMQ are obtained if the reaction according to the invention is carried out in the presence of a copper(II) halide and an alkaline earth metal chloride or an alkali metal chloride as the catalyst system.

Particularly suitable copper(II) halides are $CuCl_2$ and $CuBr_2$.

The alkaline earth metal halides added for increasing activity are essentially $MgCl_2$, $MgBr_2$, $CaCl_2$ and $CaBr_2$, in particular $MgCl_2$ and $CaCl_2$.

Particular examples of activity-increasing alkali metal halides are LiCl, LiBr, NaCl and NaBr, in particular LiCl and NaCl.

The two components of the catalyst system, the copper(II) halide and the alkaline earth metal or alkali metal halide, are added to the reaction mixture in the form of their aqueous solution or are both dissolved in the aqueous phase of the reaction mixture. The aqueous catalyst-containing solution can thus be prepared in a very simple manner. Expensive preparation of a complex catalyst beforehand, as described in European Patents 127,888 and 167,153, is not necessary.

The concentration of the copper halide in water may be from 5 to 70, preferably from 10 to 50, % by weight. The alkali metal or alkaline earth metal halides are preferably used in concentrations of from 5 to 80% by weight.

The amount of copper(II) halide is from 0.1 to 10, preferably from 0.4 to 2, moles per mole of TMP used. The alkali metal or alkaline earth metal halides are used in an amount of from 0.1 to 10, preferably from 0.5 to 5, moles per mole of TMP.

In addition to the alkali metal or alkaline earth metal halides, other activators known from the prior art, especially copper(I) salts, may also be used.

The reaction can be carried out batchwise or continuously.

To carry out the reaction, the TMP is dissolved in the alcohol component of the solvent system. The alcohol has to be melted for this purpose. Depending on the melting point of the alcohol used and the melting point depression due to the dissolution of TMP, the TMP solutions are solid or liquid at room temperature and may have to be handled at higher temperatures. The concentration of TMP in the alcohol solution is in general from 5 to 80, preferably from 10 to 50, % by weight. The ratio of aqueous phase to alcohol phase may vary from 10:1 to 1:10, preferably from 3:1 to 1:3.

Pure oxygen or an oxygen-containing gas, such as air, can be used as the oxidizing agent.

There are 2 possible methods for the addition of the alcoholic TMP solution to the aqueous catalyst solution. The total amount is either added immediately at the beginning of the reaction or slowly added dropwise during the reaction.

The reaction temperature is in principle not limited to a narrow range. It depends on the requirements for the difference relative to the flashpoint of the particular alcohol, from the point of view of plant safety. However, a particular advantage of this invention is that the difference between the reaction temperature and the flashpoint of the solvent used is over 40° C. and can therefore be chosen to be substantially higher than in previous known processes. Examples of preferred temperatures are shown in Table 2. In principle, any saturated, aliphatic alcohol which, owing to its molecular weight, has a sufficiently high boiling point and flashpoint is suitable as a solvent. The alcohols which are listed in Table 2 and are prepared on a large scale industrially from vegetable fatty acids and therefore are available in large amounts are preferred.

The Examples which follow will illustrate the invention without restricting it.

EXAMPLES 1 TO 8

A solution of the amounts, shown in Table 3, of copper(II) halide and alkali metal or alkaline earth metal halide in 100 g of water was initially taken in a 500 ml glass flask, the solution was heated by means of a water bath to the temperature stated in Table 3 and the gas space of the apparatus was evacuated twice and flushed with oxygen. Thereafter, a solution of 34 g (0.25 mole) of TMP in 100 g of the alcohol stated in Table 3 was either added immediately and all at once or was added dropwise in the course of 3 hours (h) to the catalyst solution. While the stated temperature was maintained, the reaction mixture was stirred by means of a magnetic stirrer at 1100 rpm and oxygen was passed from a gas burette into the gas space of the glass flask so that the course of the reaction could be monitored on the basis of the oxygen consumption. After the end of the absorption of oxygen, the organic phase was separated from the aqueous phase and washed twice from 60° to 70° C. with water and the yield was determined by gas chromatography using an internal standard. The TMP conversion was 100% in all cases.

TABLE 3

| Example No. | Alcohol | Reaction temperature [°C.] | Catalyst [Molar amount] | | TMP/Alcohol addition time [min] | O2 absorption time [min] | TMQ yield [% of theory] |
| --- | --- | --- | --- | --- | --- | --- | --- |
| 1 | 1-Dodecanol | 80 | $CuCl_2$ $MgCl_2$ | (0.25) (0.125) | 180 | 220 | 94.1 |
| 2 | 1-Dodecanol | 80 | $CuCl_2$ $MgCl_2$ | (0.25) (0.25) | 180 | 210 | 94.9 |
| 3 | 1-Dodecanol | 80 | $CuCl_2$ $CaCl_2$ | (0.25) (0.25) | 180 | 210 | 84.9 |
| 4 | 1-Dodecanol | 80 | $CuCl_2$ $CaCl_2$ | (0.25) (0.25) | Immediate | 70 | 82 |
| 5 | 1-Dodecanol | 80 | $CuCl_2$ LiCl | (0.25) (0.50) | 180 | 210 | 93.4 |
| 6 | 1-Dodecanol | 80 | $CuCl_2$ LiCl | (0.25) (0.50) | Immediate | 60 | 81.1 |
| 7 | 1-Hexadecanol | 90 | $CuCl_2$ LiCl | (0.25) (0.50) | Immediate | 80 | 83.9 |
| 8 | 1-Octadecanol | 90 | $CuCl_2$ LiCl | (0.25) (0.50) | Immediate | 90 | 83.4 |
| 9 | 1-Hexadecanol | 80 | $CuCl_2$ $MgCl_2$ | (0.25) (0.25) | 180 | 220 | 92 |
| 10 | 1-Dodecanol | 80 | $CuCl_2$ LiBr | (0.25) (0.25) | 180 | 210 | 94 |

We claim:

1. A process for the preparation off 2,3,5-trimethyl-p-benzoquinone by oxidation of 2,3,6-trimethylphenol with oxygen or an oxygen-containing gas in the presence of a catalyst containing a copper (II) halide, in a two-phase reaction medium consisting of an aqueous catalyst solution and a solution of 2,3,6-trimethylphenol in an aliphatic alcohol, at elevated temperatures, wherein the reaction is carried out in a mixture of water and a saturated aliphatic alcohol of 12 to 18 carbon atoms, having a flashpoint greater than 120° C., and at from 60° to 100° C.

2. A process for the preparation of 2,3,5-trimethyl-p-benzoquinone as claimed in claim 1, wherein the reaction is carried out in a mixture of water and 1-dodecanol, 1-tetradecanol, 1-hexadecanol or 1-octadecanol.

3. A process for the preparation of 2,3,5-trimethyl-p-benzoquinone as claimed in claim 1, wherein the reaction is carried out in a mixture of water and 1-dodecanol.

4. A process for the preparation of 2,3,5-trimethyl-p-benzoquinone as claimed in claim 1, wherein the reaction is carried out in the presence of a copper(II) halide and an alkaline earth metal halide as the catalyst system.

5. A process for the preparation of 2,3,5-trimethyl-p-benzoquinone as claimed in claim 4, wherein the alkaline earth metal halide used is magnesium chloride or calcium chloride.

6. A process for the preparation of 2,3,5-trimethyl-p-benzoquinone as claimed in claim 1, wherein the reaction is carried out in the presence of a copper(II) halide and an alkali metal halide as the catalyst system.

7. A process for the preparation of 2,3,5-trimethyl-p-benzoquinone as claimed in claim 6, wherein the alkali metal halide used is lithium chloride or sodium chloride.

8. A process for the preparation of 2,3,5-trimethyl-p-benzoquinone as claimed in claim 1, wherein the alcoholic solution of trimethylphenol is slowly added dropwise to the aqueous catalyst solution during the reaction.

* * * * *